(12) United States Patent
Kimura et al.

(10) Patent No.: US 7,153,502 B2
(45) Date of Patent: *Dec. 26, 2006

(54) **FOOD OR DRINK PRODUCT WITH A DISINFECTION PROPERTY OF *HELICOBACTER PYLORI***

(75) Inventors: Katsunori Kimura, Saitama-ken (JP); Haruhisa Hirata, Kanagawa-ken (JP); Yasuhiro Koga, Kanagawa-ken (JP)

(73) Assignee: Meiji Dairies Corporation, Tokyo (JP)

( * ) Notice: Subject to any disclaimer, the term of this patent is extended or adjusted under 35 U.S.C. 154(b) by 316 days.

This patent is subject to a terminal disclaimer.

(21) Appl. No.: 10/366,401

(22) Filed: Feb. 14, 2003

(65) Prior Publication Data

US 2003/0161820 A1    Aug. 28, 2003

Related U.S. Application Data

(63) Continuation of application No. 09/600,165, filed on Sep. 22, 2000, now Pat. No. 6,596,530, which is a continuation of application No. PCT/JP00/00294, filed on Jan. 21, 2000.

(30) Foreign Application Priority Data

Jun. 24, 1999    (JP) ................................ 11-178377

(51) Int. Cl.
*C12N 1/20*    (2006.01)
(52) U.S. Cl. ................. 424/93.45; 424/439; 435/252.3
(58) Field of Classification Search ...................... None
See application file for complete search history.

(56) References Cited

U.S. PATENT DOCUMENTS

| | | | |
|---|---|---|---|
| 3,767,528 | A | 10/1973 | Nagasaki et al. |
| 4,562,151 | A | 12/1985 | Kishore |
| 5,578,302 | A | 11/1996 | Brassart et al. |
| 5,981,239 | A | 11/1999 | Liu |

FOREIGN PATENT DOCUMENTS

| | | |
|---|---|---|
| EP | 0 152 235 | 8/1985 |
| EP | 0 167 411 | 1/1986 |
| EP | 0 344 786 | 12/1989 |
| EP | 0 577 903 | 1/1994 |
| EP | 0 877 032 | 11/1998 |
| EP | 1 082 964 | 3/2001 |
| GB | 1 265 773 | 3/1972 |
| JP | 6-98782 | 4/1994 |
| JP | A 6-98782 | 4/1994 |
| JP | 9-241173 | 9/1997 |
| JP | 10-130164 | 5/1998 |
| JP | 10-215813 | 8/1998 |
| JP | 10-287585 | 10/1998 |
| JP | 11-12172 | 1/1999 |
| JP | 11-106335 | 4/1999 |
| WO | WO99/64023 | 12/1999 |

OTHER PUBLICATIONS

Pedrosa et al., American Journal of Clinical Nutrition, vol. 61, 353-359, 1995.*
Mrda, et al. (1998). Therapy of Helicobacter pylori infection using Lactobacillus acidophilus. Meditsinski Pregled 51, 343-5.*
ATCC Catalogue of Bacteria, 1996, p. 195.*
Michetti et al., Digestion, 1999, 60(3), 203-9.*
Patent Abstracts of Japan. vol. 012, No. 410 (C-540), Oct. 28, 1988.
J.R. Warren, et al., The Lancet, vol. 1, No. 8336, pp. 1273-1275, "Unidentified Curved Bacilli on Gastric Epithelium in Active Chronic Gastritis," Jun. 4, 1983.
Takeshi Watanabe, et al., Gastroenterology, vol. 115, No. 3, pp. 642,648, "Helicobacter Pylori Infection Induces Gastric Cancern in Mongolian Gerbils," Sep. 1998.
F. Bazzoli, et al., Gastroenterology, vol. 102, No. 4, p. A38, "In Vivo Helicobacter Pylori Clearance Failure With Lactobacillus Acidophilus," 1992.
P. Michetti, et al., Gastroenterology, vol. 108, No. 4, p. A166, "L. Acidophilus Supernatant as an Adjuvant in the Therapy of H. Pylori in Humans," 1995.
A.L. McCartney, et al., Microbial Ecology in Health and Disease, Short Communications, vol. 8, pp. 79-84, "Ribotyping of Bifidobacterium Strains Using Cells Embedded in Agarose Plus and a 16S rDNA Prob," 1995.
Anne L. McCartney, et al., Applied and Environmental Microbiology, vol. 62, No. 12, pp. 4608-4613, "Molecular Analysis of the Composition of the Bifidobacterial and Lactobacillus Microflora of Humans," Dec. 1996.
Dominique Granato, et al., Applied and Environmental Microbiology, vol. 65, No. 3 pp. 1071-1077, "Cell Surface-Associated Lipoteichoic Acid Acts as an Adhesion Factor for Attachment of Lactobacillus Johnsonll La1 to Human Enterocyte-Like Caco-2 Cells," Mar. 1999.
T. Mitsuoka, Journal of Japanese Study Group for Lactic Acid Bacteria, vol. 2, No. 1, 5 pages, "Incomprehensive Taxonomy of Bacteria," Sep. 1991 (with English translation).
H. Ohtani, Function of Fermented Dairy Products, pp. 219-331, "Diary Products for Remedical Foods and Preventive Foods," 1998 (with partial English translation).

(Continued)

*Primary Examiner*—Irene Marx
(74) *Attorney, Agent, or Firm*—Oblon, Spivak, McClelland, Maier & Neustadt, P.C.

(57) ABSTRACT

A food or drink product with a disinfection property of *Helicobacter pylori* and/or a protection property against infection with *H. pylori*, comprising as the effective ingredient *Lactobacillus gasseri* OLL 2716 (FERM BP-6999) with a high disinfection potency of *H. pylori*.

The food or drink product prepared by using the lactic acid bacterium, such as acid milk and the like, is suitable for long-term ingestion as a food or drink product with a disinfection property of *H. pylori* and/or a protection property against infection with *H. pylori*.

10 Claims, 1 Drawing Sheet

OTHER PUBLICATIONS

Z. Mrda, et al., Med Pregl, LI (7-8), pp. 343-345, "Terapija Helicobacter Pylori Infekcije Primenom Lactobacillusa Acidophilus," 1998 (with English summary).

Official Journal of the American Gastroenterological Association, vol. 114, No. 4, Part 2, 2 pages, "Gastroenteroloy," Apr. 15, 1998.

R.I. Dave, et al., Int. Diary Journal, vol. 7, pp. 31-41, "Viability of Yoghurt and Probiotic Bacteria in Yoghurts Made From Commercial Starter Cultures," 1997.

M.C. Pedrosa, et al., Am. J. Clin. Nutr., vol. 61, No. 2, 1 page, "Survival of Yoguart-Containing Organisms and Lactobacillus Gasseri (ADH) and Their Effect on Bacterial Enzyme Activity in the Gastrointestinal Tract of Healthy and Hypochlorhydric Elderly Subjects," Feb. 1995 (English Abstract only).

ATCC Catalogue of Bacteria, p. 195, 1996.

* cited by examiner

FOOD OR DRINK PRODUCT WITH A DISINFECTION PROPERTY OF HELICOBACTER PYLORI

CROSS-REFERENCE TO RELATED APPLICATIONS

The present application is a continuation of U.S. application Ser. No. 09/600,165 filed Sep. 22, 2000, now U.S. Pat. No. 6,596,530, which is a 371 application of PCT/JP00/00294 filed Jan. 21, 2000.

DETAILED DESCRIPTION OF THE INVENTION

1. Technical Field to Which the Invention Belongs

The present invention relates to *Lactobacillus gasseri* (sometimes referred to as *L. gasseri* hereinafter) with an effect on the disinfection of Helicobacter pylori (sometimes referred to as *H. pylori* hereinafter) and/or the protection against infection with *H. pylori*, and a food or drink product containing the lactic acid bacterium.

2. Prior Art

Since the discovery of *H. pylori* as a bacterium living in stomach in 1983 by Warren et al. [Lancet, I. 1273 (1983)], attention has been focused on the relation with chronic gastritis, gastric ulcer and duodenal ulcer. Recently, it has been evidenced that gastric gland cancer occurs in mongolian gerbil infected with *H. pylori*, with no administration of any carcinogenic substance [Watanabe et al., Gastroenterology, 115; 642 (1988)] and the relation of *H. pylori* with gastric cancer has also been suggested as one etiological bacterium thereof.

Meanwhile, it is increasingly indicated that the disinfection of *H. pylori* in *H. pylori*-positive patients with digestive ulcer can suppress the recurrence of digestive ulcer and therefore, active disinfection therapy of *H. pylori* has been practiced in European counties and the U.S. As to the method for disinfecting *H. pylori*, a combination method of antibiotics (β-lactams, aminoglycosides, macrolides, tetracyclines and the like) and antiulcerative agents is general; for example, a combination therapy of three drugs, namely two types of antibiotics (clarithromycin-metronidazole or amoxycilin) and a proton pump inhibitor (PPI) suppressing the secretion of gastric acid, is clinically practiced. However, the most serious drawback of the administration of drugs such as antibiotics for the purpose of the disinfection therapy is the increase of the frequency of the occurrence of drug-resistant *H. pylori* and the occurrence of severe side effects such as diarrhea and allergy and the like, due to the multiple combination of high-dose drugs.

For the purpose of the disinfection of *H. pylori* in stomach in place of antibiotics, examinations have been made about the method comprising administering lactoferrin (Japanese Patent Laid-open 130164/1998), the method using specific antigens recovered by the immunization of chicken with the urease and flagellum of *H. pylori* as antigens (Japanese Patent Laid-open 287585/1998), and the methods comprising administering the viable bacteria of specific individual bacterial strains of *Lactobacillus* brevis and/or Lactobacillus salivarius (Japanese Patent Laid-open 241173/1997) and *Lactobacillus acidophilus* (Japanese Patent Laid-open 98782/1994), as methods using lactic acid bacteria. However, no satisfactory method has been reported yet.

On the other hand, since lactic acid bacteria generate preferable flavorful substances and have abilities to generate antibacterial substances such as lactic acid and bacteriocin, lactic acid bacteria are extremely safe microorganisms on traditional diets in the form of fermented milk and the like worldwide. Accordingly, it can be said that the disinfection of *H. pylori* utilizing the antibacterial action of lactic acid bacteria is a simple and effective method with no occurrence of side effects.

In the existing inventions, however, the selection of lactic acid bacterial strains, particularly *Lactobacillus brevis* and/or *Lactobacillus salivarius* (Japanese Patent Laid-open 241173/1997) has been carried out, not only with no consideration of the characteristic property of stomach environment (with resistance to the environment at low pH) as the target site of *H. pylori* but also with no attention paid on the properties (the survival, flavor, physical properties of the lactic acid bacterial strains) as food products prepared by using such lactic acid bacterial strains, such as fermented milk. Additionally, a report tells that *Lactobacillus acidophilus* used at a clinical test was consequently ineffective [Bazzoli et al., Gastroenterology, 102, No. 4, A38, (1992)]. Alternatively, the results of a clinical test using the culture supernatant of the bacterial strain *L. acidophilus* La1 disclosed in Japanese Patent Laid-open 98782/1994 indicate a possibility of the disinfection of *H. pylori* but never demonstrate that the effect might be sustained [Michetti et al., Gastroenterology, 108, No. 4, A166, (1995)]. As described above, the existing lactic acid bacteria have currently more rooms to be modified so as to prepare the intended composition for the disinfection of *H. pylori*.

PROBLEMS THAT THE INVENTION IS TO SOLVE

In such current status of the industry demanding the establishment of a system for the disinfection of *H. pylori*/the protection against infection with *H. pylori* in respect to anti-gastritis and anti-gastric ulcer, the present inventors have again drawn their attention toward lactic acid bacteria from the standpoints of safety profile and oral intake and have intended to develop a system for the disinfection of H. pylori/the protection against infection with *H. pylori* by using lactic acid bacteria.

More specifically, the problems to be solved by the invention are to select a lactic acid bacterial strain with high survival and a great colonization property in stomach, an apparent anti-*H. pylori* activity in animal model experiments and marked properties (the survival, flavor and physical properties of the lactic acid bacterial strain) for use in food products such as fermented milk and provide a new food or drink product, inexpensive and daily ingestible, using the lactic acid bacterial strain, for the purpose of the disinfection of *H. pylori* and the protection against infection with *H. pylori*.

MEANS FOR SOLVING THE PROBLEMS

Figure 1:
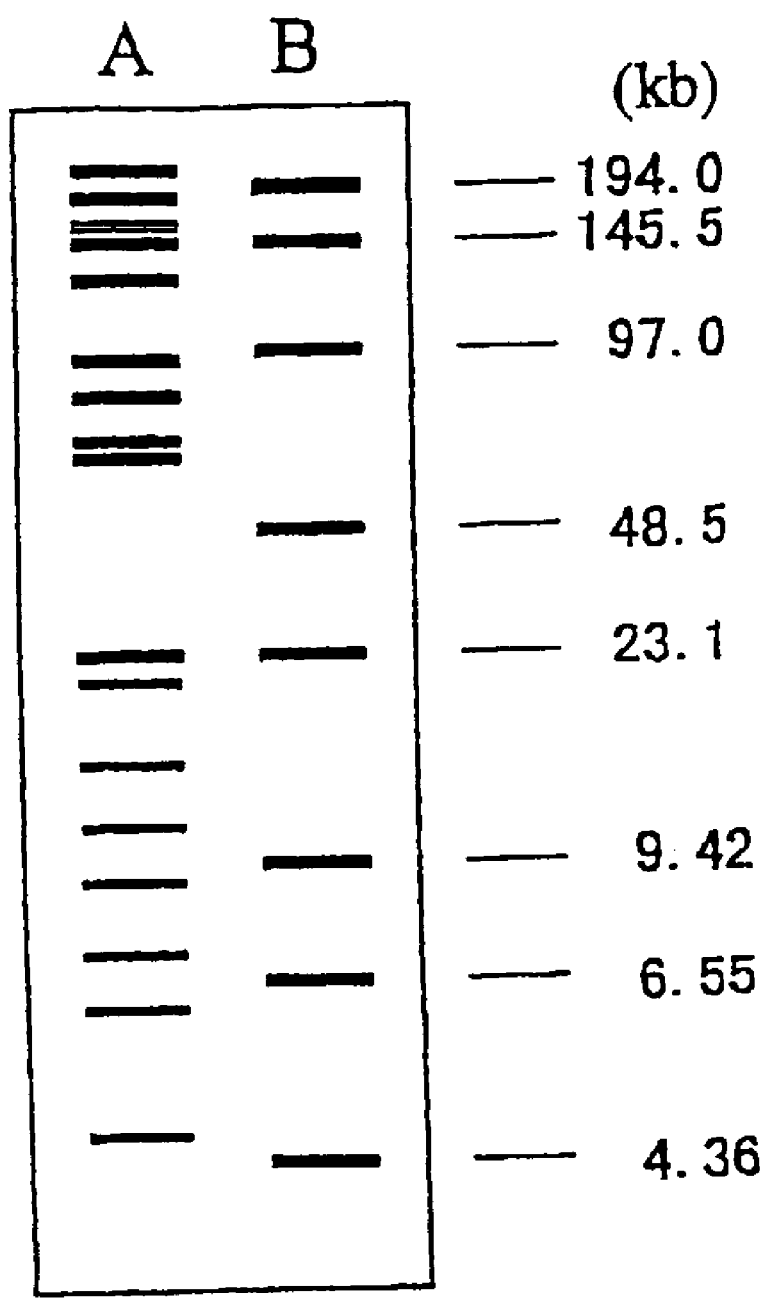
FIG. 1 shows the Apa I digested patterns (pulse field electrophoresis) of *Lactobacillus gasseri* OLL 2716 genome DNA.

The invention has been achieved so as to solve the above-mentioned problems. For the screening of the intended lactic acid bacteria, the inventors have set the following standard and have worked for the screening with efforts. More specifically, the inventors have made research works to screen a bacterial strain with the following properties among a great number of lactobacillus bacteria derived from human intestine: 1. high resistance to gastric acid; 2. good growth under conditions at low pH; 3. high potency to suppress the adherence of H. pylori on human gastric cancer cell MKN45; 4. high potency to suppress the growth of H. pylori during culture with H. pylori in mixture; 5. high-potency to disinfect H. pylori when dosed in H. pylori-infected model mouse; and 6. high survival when applied to food products, and good flavor and great physical properties. The inventors have found Lactobacillus gasseri strain OLL 2716 as a bacterial strain satisfying these conditions (the bacterial strain is deposited as FERM BP-6999 at National Institute of Bioscience and Human-Technology, Agency of Industrial Science and Technology). The bacteriological properties of the bacterial strain are as follows.

A. Morphological Properties
Cell morphology: bacillus.
Mobility: none.
Presence or absence of spore: absent.
Gram staining: positive.

B. Physiological Properties (Positive: +; Negative: −; Slightly Positive: W)
Catalase −
Gas generation −
Growth at 15° C. −
Assimilation of gluconic acid −
Optical rotation of lactic acid DL
Aerobic growth +

C. Fermentation Property of Carbohydrate (Positive: +; Negative: −; Slightly Positive: W)
Arabinose−
Xylose −
Rhamnose −
Ribose −
Glucose +
Mannose +
Fructose +
Galactose +
Sucrose +
Cellobiose +
Lactose +
Trehalose +
Melibiose −
Raffinose −
Melezitose −
Starch W
Mannitol −
Sorbitol −
Dextrin W D. Genetic Properties The content of guanine (G)+cytosine (C) in DNA is 36.4%. Additionally, according to the method of Tannock et al. [Microbial. Ecol. Health Dis., 8:79–84, 1995; Appl. Environ. Microbiol., 62: 4608–4613, (1996)]; L. gasseri OLL 2716 was cultured; the bacteria were fixed in agarose plug and then solubilized; the genome DNA was digested with restriction endonuclease (Apa I) and subjected to pulsed-field gel electrophoresis (CHEF-DR II BIO-RAD), to recover the band pattern shown in FIG. 1. In the figure, A expresses the L. gasseri strain OLL 2716; and B expresses size marker.

E. Gastric Acid Resistance

Gastric acid resistance test was conducted as follows. That is, 1 ml of a bacterial suspension of the L. gasseri strain OLL 2716 cultured twice in MRS Broth (DIFCO) under activation (37° C., 18 hours) and rinsed twice in physiological saline was added to 9 ml of an artificial gastric juice [0.2% NaCl, 0.35% pepsin (1:5000) dissolved in distilled water], pH 2.0 sterilized by filtration, for aerobic contact at 37° C. for 2 hours; thereafter, 1 ml was added to 9 ml of phosphate buffer (67 mM), pH 6.5 to terminate the reaction. Then, the number of the initial bacteria and the number of the bacteria after contact to the artificial gastric juice were counted by using MRS agar, to calculate the survival rate. The gastric acid resistance of the L. gasseri strain OLL 2716 was the highest among lactobacillus bacteria (150 strains) derived from human intestine and on comparison with the gastric acid resistance of other bacterial strains, the gastric juice resistance of the L. gasseri strain OLL 2716 was the highest (Table 1).

TABLE 1

Resistance of various lactobacillus bacteria against artificial gastric juice

| Bacterial strains | Survival rate after 2-hr treatment (%) |
| --- | --- |
| Lactobacillus gasseri OLL 2716 | 0.53 |
| Lactobacillus acidophilus JCM 11 32T | 0.48 |
| Lactobacillus rhamnosus GG (ATCC 53103) | 0.018 |
| Lactobacillus salivarius WB 1004 (FERM P-15360) | 0.004 |
| Lactobacillus brevis WB 1005 (FERM P-15361) | 0.18 |

E. Growth Under Conditions at Low pH

10 µl of the L. gasseri strain OLL 2716 cultured twice under activation in MRS Broth (37° C., 18 hours) was inoculated on a modified MRS Broth [0.2% NaCl, 0.35% pepsin (1:5000) dissolved in MRS Broth and adjusted to pH 4.0] and aerobically cultured therein at 37° C. Nine hours after the start of culturing, the turbidity ($OD_{650}$) of the culture medium was measured as growth degree. Consequently, the L. gasseri strain OLL 2716 was at the highest growth under conditions at low pH (Table 2).

TABLE 2

Growth of various lactobacillus bacteria under conditions at low pH

| Bacterial strains | $OD_{650}$ 9 hours after culturing |
| --- | --- |
| Lactobacillus gasseri OLL 2716 | 0.255 |
| Lactobacillus acidophilus JCM 1132T | 0.030 |
| Lactobacillus rhamnosus GG (ATCC 53103) | 0.222 |
| Lactobacillus salivarius JCM 1231 | 0.116 |

G. Adherence Potency on Human Gastric Cancer Cell (MKN45)

The adherence potencies of the L. gasseri strain OLL 2716 and L. acidophilus CNCM I-1225 on human gastric cancer cell MKN45 were examined according to the method of Granato et al. [Appl. Environ. Microbiol., 65(3), 1071–1077, (1999)] who examined the adherence potency of lactic acid bacteria on human large intestine cancer cell. MKN45 was cultured at 37° C. for 3 days, by using 10 ml of an RPMI 1640 culture medium (RPMI, Nissui Pharmaceuticals) containing 10% FCS. After culturing, the cells were scaled off and rinsed in RPMI, and were then suspended in RPMI to a final cell concentration of $5 \times 10^4$ cells/ml and then divided at 0.1 ml/well in a 96-well microplate. After additional culturing at 37° C. for 3 days, MKN45 adhered on the microplate was rinsed in 0.1M phosphate buffer, pH 6, to prepare a monolayer of MKN45. 0.1 ml of a suspension of the L. gasseri strain OLL 2716 or L. acidophilus CNCM I-1225 cultured in MRS broth (DIFCO) and subsequently suspended in 0.1M phosphate buffer, pH 6 to final $10^9$ CFU/ml was added to the monolayer; and the resulting mixture was incubated at 37° C. for 30 minutes. The monolayer of MKN45 was rinsed three times in 0.1M phosphate buffer, pH6; and then, the lactic acid bacteria never adhered were removed. The lactic acid bacteria adhered on MKN45 were Gram stained and the number thereof was counted by using a microscope. Consequently, it was observed that the bacterial number of the L. gasseri strain OLL 2716 adhered on MKN45 was larger than that of L. acidophilus CNCM I-1225. In other words, it was confirmed that the L. gasseri strain OLL 2716 had a high adherence potency on the human gastric cancer cell (Table 3).

TABLE 3

Adherence potency of Lactobacillus gasseri strain OLL 2716 on human gastric cancer cell

| | Number of adhered bacteria per 100 cells of MKN45 (mean ± standard deviation) |
|---|---|
| Lactobacillus gasseri OLL 2716 | 560 ± 55** |
| Lactobacillus acidophilus CNCM I-1225 | 234 ± 30 |

**$p < 0.01$ (Student's t test, n = 4)

The L. gasseri strain OLL 2716 was selected as a bacterial strain having high gastric acid resistance in human stomach environment, growing well under conditions at low pH and being capable of disinfecting H. pylori and protecting hosts against infection with H. pylori by the administration of the viable bacteria of the bacterial strain in the forms of pharmaceutical agents (anti-gastritis agent, anti-ulcer agent) or food products (fermented milk, liquid form, paste form, dried product), thereby preventing the onset or recurrence of gastritis or gastric or duodenal ulcer. Accordingly, the anti-H. pylori activity of the L. gasseri strain OLL 2716, the yogurt production properties (shelf life, flavor, physical properties) thereof, and the effect of the L. gasseri strain OLL 2716 on the disinfection of H. pylori when dosed in H. pylori-infected model mouse are described in detail with reference to examples, but the invention is not limited to these.

More specifically, the invention relates to a food product with a disinfection property of H. pylori and/or a protection property against infection with H. pylori, comprising at least one of a lactic acid bacterium belonging to Lactobacillus gasseri with a high disinfection potency of Helicobacter pylori, a material containing the lactic acid bacterium, and a processed product thereof.

The material containing the lactic acid bacterium includes the suspension of the lactic acid bacterium; the culture of the lactic acid bacterium (including the bacteria, culture supernatant, culture medium components); the liquid culture of the lactic acid bacterium prepared by discarding solids from the culture of the lactic acid bacterium; the lactic acid bacterium-fermented milk comprising a food or drink product prepared by fermenting the lactic acid bacterium, such as lactic acid bacterial drink, acid milk and yogurt; and the like.

The processed product includes the concentrates of the lactic acid bacterium, materials containing the lactic acid bacterium, and the fermented milk; the paste products thereof; the dried products (spray-dried products, freeze-dried products, vacuum-dried products, drum-dried products and the like) thereof; the liquid products thereof; the dilution products thereof; and the like. As the lactic acid bacterium, additionally, viable bacteria, wet bacteria, dried bacteria and the like can be appropriately used.

The food or drink product of the invention contains at least one of the lactic acid bacterium, a material containing the same and a processed product thereof as the effective ingredient and is also useful as health food.

The amount of the effective ingredient to be blended is arbitrary and can be determined appropriately, depending on the purpose of the use (prophylaxis, health or therapeutic treatment) thereof. Generally, the amount within a range of 0.0001 to 10% is appropriate. For long-term intake for the purpose of health and hygiene or for the purpose of health control, however, the amount may be below the above-mentioned range; and since the effective ingredient has no problem in terms of safety profile, it can absolutely be used at an amount above the range. The results of an acute toxicity test thereof in mice for 10 days demonstrate actually that no death was observed at an oral dosing of 5,000 mg/kg/day.

The effective ingredient can be used as it is in food or drink products or can be used in combination with other food materials and food components appropriately in conventional manners. The composition of the invention using the effective ingredient may take any form of paste, liquid and suspension, but preferably, the composition is prepared as health drinks, by using sweeteners, sour agents, vitamins and other various components for routine use in the production of drinks.

In accordance with the invention, the viable bacteria of the L. gasseri strain OLL 2716 can be ingested for example in the forms of fermented milk, mainly including yogurt (plain yogurt, fruit yogurt, dessert yogurt, drink yogurt, and frozen yogurt), lactic acid bacteria drinks, powdery food products, granule food products, paste food products and the like. The L. gasseri strain OLL 2716 is excellent particularly in terms of production properties (shelf life, flavor, physical properties) when the strain is used for the preparation of fermented milk, as described below. Therefore, the method for administering the L. gasseri strain OLL 2716 in the form of fermented milk is the most desirable. For the preparation of fermented milk, a method is effective using lactic acid bacteria of genera Lactobacillus, Streptococcus, Leuconostoc, Pediococcus and the like, bifidobacteria of Bifidobacterium longum, B. breve, B. infantis, B. bifidum and the like, and yeast and the like, together with the L. gasseri strain OLL 2716 as a starter. Additionally, the L. gasseri strain OLL 2716 for the preparation of fermented milk can also be utilized for the method comprising sequentially preparing stock culture, mother starter and bulk starter in this order and can be utilized as concentrate starter (frozen product or freeze-dried product) of a larger bacterial number, which is directly inoculated for bulk starter or product production, with no preparation process of mother starter.

TEST EXAMPLE 1

The adherence of H. pylori strain NCTC 11637 on human gastric cancer cell (MKN45) was suppressed by the L. gasseri strain OLL 2716 according to the method of Kabir et al. [Gut, 41(1); 49–55, (1997)].

In order to prepare a fluorescence-labeled bacterial solution of the H. pylori strain CNTC 11637, first, the H. pylori strain NCTC 11637 cultured twice under activation (37° C. for 72 hours) in Brucella broth (DIFCO) containing 5% FCS (fetal calf serum) under slightly aerobic conditions was rinsed in PBS and was thereafter suspended in Diluent A of a cell fluorescence-labeling kit PKH-2 (Dai-Nippon Pharmaceuticals, Co.) to a final $OD_{650}$ of 2.0. Slightly aerobic culturing was effected by using a gas generation bag Aneropack Helico (Mitsubishi Gas Chemicals, Co.) for culturing Helicobacter. To 1 ml of the suspension was added 50 μl of a fluorescence-labeling dye PKH-2, for reaction at room temperature for 15 minutes; thereafter, the bacteria were recovered by centrifugation (3,000 rpm, 10 minutes), rinsed in Hank's balanced salt solution (HGS) and suspended in 1 ml of HGS; and the resulting solution was designated a fluorescence-labeled bacterial solution. Then, 0.1 ml of the fluorescence-labeled bacterial solution ($OD_{650}$=2.0) of the *H pylori* strain NCTC 11637 and 0.1 ml of the bacterial solution ($OD_{650}$=4.0) of the *L. gasseri* strain OLL 2716 were simultaneously added to 0.8 ml of a cell suspension ($1 \times 10^6$ cells/ml) of MKN45, for shaking aerobically at 37° C. for 1 hour. The cell suspension of MKN45 was used singly as a blank (0.8 ml of the cell suspension of MKN45+0.2 ml HGS); a solution with addition of HGS in place of the bacterial solution of the *L. gasseri* strain OLL 2716 was used as a negative control. After shaking, 9 ml of Dulbecco's PBS containing 15% sucrose [Cell Culture Technique (the sixth edition), Asakura Shoten, pp. 20 (1991)] was added, and the cell was harvested by centrifugation (1,000 rpm, 10 minutes) and rinsed in HGS and centrifuged (1,000 rpm, 10 minutes); subsequently, the resulting cell was again suspended in 1 ml of HGS; 250 μl of the resulting suspension was added to the well of a 96-well microplate for fluorescence assay; and the fluorescence intensity (excitation wave length: 490 nm, measuring wave length: 530 nm) was measured with a fluorescence plate reader.

Provided that the adherence ratio of the *H. pylori* strain NCTC 11637 alone on gastric cancer cell was designated 100%, consequently, the adherence ratio of the *H. pylori* strain NCTC 11637 in the system with addition of the *L. gasseri* strain OLL 2716 was 92.8%; thus, it was confirmed that the bacterial strain had an effect to suppress the adherence of *H. pylori* on gastric cancer cell.

TEST EXAMPLE 2

At a test of the suppression of the growth of the *H. pylori* strain NCTC 11637 by the *L. gasseri* strain OLL 2716, the *H. pylori* strain NCTC 11637 and the *L. gasseri* strain OLL 2716 were cultured twice under activation and inoculated in 200 ml of Brucella broth (DIFCO) containing 5% FCS at final $10^6$ colony forming units (CFU)/ml and $10^5$CFU/ml, respectively, for culturing at 37° C. under slightly aerobic conditions. The numbers of the viable bacteria of the *H. pylori* strain NCTC 11637 and the *L. gasseri* strain OLL 2716 were counted 0, 24, and 48 hours after the start of culturing. For the detection of the *H. pylori* strain NCTC 11637 and the *L. gasseri* strain OLL 2716, a modified Skirrow culture medium [horse blood (7%), BHIagar (52 g), trimethoprim (5 mg/l), polymyxinB (2,500 U/ml), vancomycin (10 mg/l), bacitracin (5 mg/l), distilled water (1,000 ml)] (37° C., 7 days, slightly aerobic culturing) and MRS agar (37° C., 48 hours, anaerobic culturing) were used, respectively.

Consequently, the number of the viable bacteria of the *H. pylori* strain NCTC 11637 was increased to about 5-fold 48 hours after culturing thereof alone, but the number of the viable bacteria thereof was decreased to about 1/10 in the case of the co-presence of the *L. gasseri* strain OLL 2716; and it was confirmed that the *L. gasseri* strain OLL 2716 had a potency to suppress the growth of the *H. pylori* strain NCTC 11637 (Table 4).

TABLE 4

Effect of *Lactobacillus gasseri* strain OLL 2716 on the suppression of the growth of *Helicobacter pylori* strain NCTC 11637

| Bacterial strains | 0 h | 24 h | 48 h |
|---|---|---|---|
| *Helicobacter pylori* NCTC 11637 | $1.5 \times 10^6$ | $3.3 \times 10^6$ | $7.9 \times 10^6$ |
| Growth ratio of *Helicobacter pylori* (%) | 100 | 220.0 | 526.7 |
| *Lactobacillus gasseri* OLL 2716 | $2.2 \times 10^5$ | $7.4 \times 10^7$ | $4.5 \times 10^7$ |
| *Helicobacter pylori* NCTC 11637 | $1.9 \times 10^6$ | $1.2 \times 10^6$ | $1.8 \times 10^5$ |
| Growth ratio of *Helicobacter pylori* (%) | 100 | 63.2 | 9.5 |

TEST EXAMPLE 3

It is demonstrated that *H. pylori* can survive under strong acid conditions because *H. pylori* has an ability to decompose urea and generate ammonia. In order to examine the potency of the *L. gasseri* strain OLL 2716 to suppress the growth of the *H. pylori* strain NCTC 11637 in the presence of urea, the effects of the bacterial strain and Lactobacillus acidophilus CNCM I-1225 to suppress the growth of the *H. pylori* strain NCTC 11637 under low pH conditions were examined. The *H. pylori* strain NCTC 11637 and the *L. gasseri* strain OLL 2716 or the *L. acidophilus* strain CNCM I-1225 were twice cultured under activation and were then inoculated in 200 ml of Brucella broth, pH 4.0 containing 5% FCS and 5 mM urea to final $10^5$ CFU/ml and $10^7$ CFU/ml, respectively, for culturing at 37° C. under slightly aerobic conditions. The numbers of the viable bacteria of the *H. pylori* strain NCTC 11637 and the *L. gasseri* strain OLL 2716 or the *L. acidophilus* strain CNCM I-1225 were counted, 0, 6 and 12 hours after the start of culturing.

As a result, 6 and 12 hours after the start of culturing, the potency of the *L. gasseri* strain OLL 2716 to suppress the growth of the *H. pylori* strain NCTC 11637 in the presence of urea was observed to be higher than the potency of the *L. acidophilus* strain CNCM I-1225. That is, it was confirmed that the bacterial strain had a high potency to suppress the growth of *H. pylori* even in the presence of urea (Table 5).

TABLE 5

Effect of *Lactobacillus gasseri* OLL 2716 to suppress the growth of *Helicobacter pylori* in the presence of urea

| Bacterial strain | 0 h | 24 h | 48 h |
|---|---|---|---|
| *Helicobacter pylori* NCTC 11637 | $2.0 \times 10^5$ | $2.0 \times 10^5$ | $1.8 \times 10^5$ |
| Growth ratio of *Helicobacter pylori* (%) | 100 | 100 | 90.0 |
| *Lactobacillus gasseri* OLL 2716 | $1.5 \times 10^7$ | $4.0 \times 10^7$ | $1.2 \times 10^8$ |
| *Helicobacter pylori* NCTC 11637 | $2.0 \times 10^5$ | $1.5 \times 10^5$ | $3.0 \times 10^4$ |
| Growth ratio of *Helicobacter pylori* (%) | 100 | 75.0 | 15.0 |
| *Lactobacillus acidophilus* CNCM I-1225 | $1.6 \times 10^7$ | $2.5 \times 10^7$ | $8.9 \times 10^7$ |
| *Helicobacter pylori* NCTC 11637 | $2.0 \times 10^5$ | $1.9 \times 10^5$ | $1.0 \times 10^5$ |
| Growth ratio of *Helicobacter pylori* (%) | 100 | 95.0 | 50.0 |

EXAMPLE 1

Plain yogurt was prepared by using the *L. gasseri* strain OLL 2716. More specifically, the *L. gasseri* strain OLL 2716, *L. bulgaricus* JCM 1002T and *S. thermophilus* ATCC 19258 were individually inoculated at 1% on a culture medium of 10% powdery skimmilk, for culturing at 37° C. for 15 hours to prepare bulk starters. To a yogurt mix (SNF: 9.5%, FAT: 3.0%) thermally treated at 95° C. for 5 minutes were inoculated 1% each of the starters of *L. bulgaricus* JCM 1002T and *S. thermophilus* ATCC 19258 and 5% of the starter of the *L. gasseri* strain OLL 2716; and the resulting yogurt mix was fermented at 43° C. for 4 hours. Immediately after fermentation and cooling, the numbers of the viable bacteria of the *L. gasseri* strain OLL 2716, *L. bulgaricus* JCM 1002T and *S. thermophilus* ATCC 19258 were $9.0 \times 10^7$ CFU/ml, $6.4 \times 10^7$ CFU/ml, and $11.0 \times 10^8$ CFU/ml, respectively, and the resulting yogurt exerted good flavor and physical properties. After the storage of the yogurt at 10° C. for 2 weeks, the numbers of the viable bacteria of the *L. gasseri* OLL 2716, *L. bulgaricus* JCM 1002T and *S. thermophilus* ATCC 19258 were $3.7 \times 10^7$ CFU/ml, $2.7 \times 10^7$ CFU/ml, and $10.8 \times 10^8$ CFU/ml, respectively, and the number of the viable bacteria of the *L. gasseri* strain OLL 2716 decreased only slightly. The flavor and physical properties of the stored product were excellent.

COMPARATIVE EXAMPLE 1

Plain yogurt was prepared by using *L. salivarius* strain WB1004 (FERMP-15360). More specifically, the same procedures as in Example 1 were carried out, except for the use of the *L. salivarius* strain WB1004 (FERM P-15360) in place of the *L. gasseri* strain OLL 2716. Immediately after fermentation and cooling, the numbers of the viable bacteria of the *L. salivarius* strain WB1004, *L. bulgaricus* JCM 1002T and *S. thermophilus* ATCC 19258 were $5.3 \times 10^7$ CFU/ml, $6.0 \times 10^7$ CFU/ml, and $12.5 \times 10^8$ CFU/ml, respectively, and the resulting yogurt exerted good flavor and physical properties. After the storage of the yogurt at 10° C. for 2 weeks, the numbers of the viable bacteria of the *L. salivarius* strain WB1004, *L. bulgaricus* JCM 1002T and *S. thermophilus* ATCC 19258 were $0.1 \times 10^7$ CFU/ml, $4.5 \times 10^7$ CFU/ml, and $8.8 \times 10^8$ CFU/ml, respectively, and the number of the viable bacteria of the *L. salivarius* strain WB1004 (FERM P-15360) was decreased to about 1/50.

Example 1 and Comparative Example 1 can be summarized as the following table.

|  | Storage | Number of viable bacteria ($\times 10^7$ CFU/ml) | | Acidity (%) | pH | Flavor |
|---|---|---|---|---|---|---|
|  |  | OLL 2716 | WB 1004 |  |  |  |
| Example 1 | prior to storage | 9.0 |  | 0.90 | 4.42 | excellent |
|  | two weeks | 3.7 |  | 1.11 | 4.07 | good |
| Comparative Example 1 | prior to storage |  | 5.3 | 0.87 | 4.40 | excellent |
|  | two weeks |  | 0.1 | 1.20 | 3.99 | strong acid taste |

TEST EXAMPLE 4

For the purpose of examining in vivo the effect of the administration of the viable bacteria of the *L. gasseri* strain OLL 2716 or the *L. salivarius* WB1004 (FERM P-15360) on *H. pylori* disinfection, the *H. pylori* strain NCTC 11637 were allowed to infect germ free mice (BALB/c) at $1 \times 10^9$ CFU/mouse; 4 weeks later, then, the *L. gasseri* strain OLL 2716 and the *L. salivarius* strain WB1004 (FERM P-15360) were individually administered to the *H. pylori*-infectedmice at $1 \times 10^9$ CFU/mouse, three times on week 1 and once per week from week 2 to week 7. Eight weeks after the administration of the viable bacteria of the *L. gasseri* strain OLL 2716 or the *L. salivarius* WB1004 (FERM P-15360), the number of *H. pylori* and the number of the *L. gasseri* strain OLL 2716 or the *L. salivarius* WB 1004 (FERM P-15360) in their stomachs were counted in the modified Skirrow culture medium and MRS agar, respectively, while serum anti-*H. pylori* antibody titer (absorbance at 492 nm) was assayed by enzyme-linked immunosorbent assay (ELISA).

Eight weeks later, consequently, the *H. pylori* number in the stomachs of the control mice (administered with *H. pylori* alone) was detected at $10^5$ CFU/g, while the *H. pylori* numbers in the stomachs of the mice administered with the viable bacteria of the *L. gasseri* strain OLL 2716 and the *L. salivarius* WB 1004 (FERM P-15360) were decreased below the detectable limits (at $10^3$ CFU/g or less). However, the anti-*H. pylori* antibody titer of the mice administered with the *L. gasseri* strain OLL 2716 was decreased to 1/5 or less, compared with the control mice, and was also decreased to 1/4 or less, compared with the anti-*H. pylori* antibody titer of the *L. salivarius* strain WB1004 (FERM P-15360) (Table 6). Thus, it was observed that the effect of the *L. gasseri* strain OLL 2716 on the disinfection of *H. pylori* was higher than that of the *L. salivarius* WB1004 (FERM P-15360). It was additionally confirmed that the *L. gasseri* strain OLL 2716 had a colonization potency in stomach, because the administered bacterial strain was detected at $10^6$/g or more in the mice on week 8 after the administration of the *L. gasseri* strain OLL 2716.

TABLE 6

Number of lactobacillus bacteria colonizing in stomach and effect on the disinfection of *Helicobacter pylori* NCTC 11637

| Mice | Bacterial number in stomach contents (Log CFU/g) | | | Anti-*H. pylori* antibody titer A492 |
|---|---|---|---|---|
|  | *L. salivarius* | *L. gasseri* | *H. pylori* |  |
| Control (N = 5, no administration of lactic acid bacteria) | no detection | no detection | 5.2 ± 0.04 | 0.488 ± 0.284* |
| *L. gasseri* strain OLL 2716 administered (N = 6) | no detection | 6.1 ± 1.0 | <3.0 | 0.086 ± 0.082* |
| *Lactobacillus salivarius* WB 1004 (FERM P-15360) administered (N = 5) | 6.1 ± 0.8 | no detection | <3.0 | 0.346 ± 0.276 |

*P < 0.05 (Scheffe test)

TEST EXAMPLE 5

For the purpose of verifying the efficacy of the *L. gasseri* strain OLL 2716 in humans, a yogurt containing the *L. gasseri* strain OLL 2716 was administered to *H. pylori*-positive 30 subjects aged 40 to 60. 90 g of the yogurt prepared in the same manner as in Example 1 was given twice daily for 8 weeks. The effect on *H. pylori* disinfection was examined by urea breath test, blood pepsinogen (I), pepsinogen (II) and endoscopy (6 subjects).

Consequently, the blood pepsinogen (I/II) ratio used as a marker of *H. pylori* disinfection was improved in 26 of 30; and at the urea breath test, improvement was observed in 21 of 28. Further, the *H. pylori* number was counted in the gastric cells in the 6 subjects enrolled in the endoscopic examination; and the results indicate that the *H. pylori* number was decreased in all of the 6 subjects to 1/10 to 1/100 the number prior to the administration.

REFERENCE EXAMPLE 1

The *L. gasseri* strain OLL 2716 was inoculated on 5 liters of MRS liquid culture medium (DIFCO), for stationary culturing at 37° C. for 18 hours. After the termination of the culturing, the culture was centrifuged at 7,000 rpm for 15 minutes, to recover a bacterial concentrate of a 1/50 the volume of the liquid culture. Then, the bacterial concentrate was mixed with an equal volume of a dispersion medium containing 10% (by weight) powdery skim milk and 1% (by weight) sodium glutamate and was then adjusted to pH 7, and the resulting mixture was subsequently freeze-dried. The resulting freeze-dried product was pulverized with a sieve of 60 mesh, to recover a freeze-dried bacterial powder.

REFERENCE EXAMPLE 2

According to the Rule "Powders", General Pharmaceutical Preparation Regulation, Guidebook of the Japanese Pharmacopoeia, the 13th revised edition, 400 g of lactose (according to JP.) and 600 g of potato starch (according to JP.) were added to and homogeneously mixed with 1 g of the freeze-dried bacterial powder of the *L. gasseri* strain OLL 2716 recovered in the aforementioned Example, to prepare a powder.

EXAMPLE 2

Skim milk was sterilized at 80 to 85° C. for 20 to 30 minutes and then homogenized, which was then cooled. To the resulting homogenate was added 2 to 5% of a pure culture of the bacterial strain (FERM BP-6999) as the starter, for fermentation at 37 to 40° C. for 16 hours, to recover an acid milk (a culture in a culture medium of skim milk) at a lactic acid content of 2%. Under disruption of the emerging curd, the acid milk was cooled at 5° C., which was designated acid milk.

On the other hand, a sugar solution containing appropriate amounts of a sour agent, flavor and a dye in addition to 15% sucrose was prepared and homogenized, sterilized at 70 to 80° C. for 20 to 30 minutes and cooled to 5° C., which was designated sugar solution.

By mixing together the sugar solution and the acid milk thus recovered at a ratio of 65:35, an acid milk drink was recovered.

EXAMPLE 3

40 g of the freeze-dried product of the culture of the bacterial strain in the culture medium of powdery skim milk as recovered in Example 1, was added to 40 g of vitamin C or 40 g of a mixture of equal amounts of vitamin C and citric acid, 100 gof granulated sugar, and 60 g of a mixture of equal amounts of corn starch and lactose, followed by sufficient blending. The mixture was packed in packages, to prepare 150 packages of a stick-type nutritious health food of 1.5 g per one package.

REFERENCE EXAMPLE 3

Based on the following composition, an anti-ulcerative agent was prepared: (1) 50 g of the freeze-dried product of the culture of the bacterial strain in the culture medium of powdery skim milk; (2) 90 g of lactose; (3) 29 g of corn starch; and (4) 1 g of magnesium stearate.

First, (1), (2) and (3) (17 g, herein) were mixed together and granulated, together with a paste prepared from (3) (7 g, herein). To the resulting granule were added (3) (5 g, herein) and (4), and the resulting mixture was thoroughly blended together; the mixture was compressed by a compression tableting machine, to prepare 100 tablets, each tablet containing 40 mg of the effective ingredient.

ADVANTAGES OF THE INVENTION

In accordance with the invention, the disinfection of *H. pylori* and/or the protection against infection with *H. pylori* can be practiced efficiently with no occurrence of side effects. The composition of the invention is absolutely not problematic in terms of safety profile and can be freely prepared in the forms of dairy products and other various food or drink products, so the composition can be ingested by healthy people as well as babies and infants, aged people, valetudinarians, and convalescents and the like for a long period of time and exerts a particularly excellent prophylactic and/or therapeutic effect on gastritis, gastric ulcer and the like.

REFERENCE TO DEPOSITED MICROORGANISM ACCORDING TO THE REGULATION, RULE NO. 13-2

1. *Lactobacillus gasseri* OLL 2716
a. The name and address of the depository organization at which the microorganism is deposited Name: National Institute of Bioscience and Human-Technology, Agency of Industrial Science and Technology, Ministry of International Trade and Industry Address: 1–3, Higashi 1-chome, Tsukuba-shi, Ibaraki-ken, Japan (T305-8566)
b. Deposition date at the depository organization May 24, 1999
c. Accession No. issued at the time of deposition by the depository organization FERM BP-6999

The invention claimed is:

1. A composition, comprising *Lactobacillus gasseri* OLL 2716, FERM BP-6999; and at least one food or drink material.

2. The composition of claim 1, which is in the form of a paste, liquid or suspension.

3. The composition of claim 2, which is in the form of a paste.

4. The composition of claim 2, which is in the form of a liquid.

5. The composition of claim 2, which is in the form of a suspension.

6. The composition of claim 1, which further comprises one or more of a sweetener, a sour agent, and a vitamin.

7. The composition of claim 1, which is a fermented milk product.

8. The composition of claim 7, wherein the fermented milk product is a yogurt.

9. The composition of claim 8, wherein the yogurt comprises fruit and/or sweetener.

10. The composition of claim 8, which is frozen yogurt.

* * * * *